United States Patent
Chambers et al.

(10) Patent No.: US 10,130,100 B2
(45) Date of Patent: Nov. 20, 2018

(54) CONTROL OF ARTHROPOD INFESTATION USING PARTICLES COMPRISING AN ENTOMOPATHOGEN AND WAX

(71) Applicant: Exosect Limited, Winchester, Hants (GB)

(72) Inventors: John Chambers, York (GB); Clare Gillian Storm, Winchester (GB); Maureen Elzabeth Wakefield, York (GB)

(73) Assignee: Exosect Limited, Winchester, Hants (GB)

( * ) Notice: Subject to any disclaimer, the term of this patent is extended or adjusted under 35 U.S.C. 154(b) by 0 days.

(21) Appl. No.: 14/665,382

(22) Filed: Mar. 23, 2015

(65) Prior Publication Data

US 2015/0189871 A1    Jul. 9, 2015

Related U.S. Application Data (63) Continuation of application No. 13/704,291, filed as application No. PCT/GB2011/000889 on Jun. 14, 2011, now abandoned.

(30) Foreign Application Priority Data

Jun. 16, 2010    (GB) .................................. 1010042.8

(51) Int. Cl.
*A01N 25/24*    (2006.01)
*A01N 63/04*    (2006.01)
*A01N 25/08*    (2006.01)

(52) U.S. Cl.
CPC ............. *A01N 63/04* (2013.01); *A01N 25/08* (2013.01); *A01N 25/24* (2013.01)

(58) Field of Classification Search
CPC ..................................................... A01N 63/04
See application file for complete search history.

(56) References Cited

U.S. PATENT DOCUMENTS

2009/0060880 A1    3/2009    Meikle et al.

FOREIGN PATENT DOCUMENTS

WO    97/33472 A1    9/1997

OTHER PUBLICATIONS

Batta, Int. J. Food Eng., 2008, 1, 9, 18 pgs.*
C. Luz & J. Fargues, "Temperature and moisture requirements for conidial germination of an isolate of *Beauveria bassiana*, pathogenic to Rhodnius prolixus", Mycopathologia, vol. 138, pp. 117-125, Aug. 5, 1997.
Jeffrey C. Lord, "Desiccation increases the efficacy of *Beauveria bassiana* for stored-grain pest insect control", Journal of Stored Products Research, 2007, pp. 535-539, vol. 43.
William G. Meikle, et al., "Impact of a treatment of *Beauveria bassiana* (Deuteromycota: Hyphomycetes) on honeybee (Apis mellifera) colony health and on Varroa destructor mites (Acari: Varroidae)", Apidologie, 2008, pp. 247-249, vol. 39.
William G. Meikle, et al., "Impact of two treatments of a formulation of *Beauveria bassiana* (Deuteromycota: Hyphomycetes) conidia on Varroa mites (Acari: Varroidae) and on honeybee (Hymenoptera: Apidae) colony health", Exp Appl Acarol, 2008, pp. 105-117, vol. 46.
M.E. Wakefield, "Factors affecting storage insect suspectibility to the entomopathogenic fungus *Beauveria bassiana*", Alternative Methods to Chemical Control, pp. 855-862.

\* cited by examiner

*Primary Examiner* — Kyle A Purdy
(74) *Attorney, Agent, or Firm* — Sughrue Mion, PLLC (57) ABSTRACT

Composite particles containing hydrophobic particles and spores of an entomopathogenic fungus that are capable of germinating on the cuticle of a grain storage arthropod, dry powder compositions comprising such composite particles, methods of producing such compositions and methods and uses thereof.

20 Claims, 3 Drawing Sheets

CONTROL OF ARTHROPOD INFESTATION USING PARTICLES COMPRISING AN ENTOMOPATHOGEN AND WAX

CROSS REFERENCE TO RELATED APPLICATIONS

This is a Continuation of application Ser. No. 13/704,291 filed Mar. 7, 2013, claiming priority based on International Application No. PCT/GB2011/000889 filed Jun. 14, 2011, claiming priority based on British Patent Application No. 1010042.8 filed Jun. 16, 2010, the contents of all of which are incorporated herein by reference in their entirety.

The present invention relates to a method of controlling arthropod infestation, composite particles, compositions for treating arthropod infestation and uses thereof. In particular, the invention relates to methods of controlling arthropod infestation in grain storage areas, methods for the application of compositions in dry powder form to arthropods, dry powder compositions comprising biological agents in association with hydrophobic particles, methods of producing such compositions, and uses thereof.

Dried food storage areas, and grain storage areas, such as grain silos and grain bins where grain is stored immediately after harvest or prior to processing attract arthropods such as mites and beetles, particularly beetles. Other dried food and grain storage areas include warehouses where dried food and grain is stored prior to shipment, and transport facilities such as those of shipping containers, the holds of ships, trucks and the like. Further dried food and grain storage areas include those in which grain products such as flours, dried beans, lentils, rice and other commodities derived from grain and/or dried food are kept. Arthropods such as insects, for example grain storage beetles, feed on the grain and are a major cause of economic losses to farmers and grain utilising industries.

When grain is removed from grain storage areas, many arthropods are left behind, inhabiting cracks and crevices in walls, floors and other support structures such as pillars and/or shelving. Conventional procedures for controlling arthropod infestations that rely on the use of chemicals applied as wet formulations to empty grain storage areas are effective insofar as they kill arthropods that come into contact with the applied chemical. However, wet chemical formulations typically do not get into cracks and crevices inhabited by populations of arthropods. Such populations survive the application of chemicals that are applied to the surfaces of the surrounding environment and are thus free to infest new shipments of grain that are deposited in the storage area, and so the cycle of grain infestation with concurrent economic losses is repeated.

Other methods of treating grain storage areas rely on the application of relatively high levels of arthropodicidal chemicals in dry powder form. However, the effectiveness of such treatments diminishes over time.

Biological agents have been used in the prior art in attempts to control infestations of various kinds of arthropods in various settings. In particular, certain strains of entomopathogenic fungi such as *Beauveria bassiana, Paecilomyces fumosoroseus* and *Lecanicillium* spp. have found use in the control of certain arthropods. Although entomopathogenic fungi are clearly seen as candidates for controlling infestations of arthropods, it is also apparent that most strains of entomopathogenic fungi are unsuitable as candidates for the control of arthropod infestations in the myriad of so-called field environments in which the effective use of strains of fungus would be desirable. Often, it has been shown that apparently suitable candidate strains of fungus are unable to tolerate the environmental extremes that often exist in man made environments, such as grain storage areas or other environments in which grain-related foodstuffs (e.g. flour) or grain may be placed.

A problem in using biological agents such as candidate strains of entomopathogenic fungus which may be discovered in one country and proposed for use in a setting in a different country is that such strains may not perform well in the new setting because they are unable to tolerate the extremes of conditions that prevail in the environment in the country in which they are to be used. In addition, regulatory constraints may be so arduous as to make the importation of a likely candidate strain unfeasible and this may be coupled with doubts about being able to prove its likely effectiveness in an exotic environment.

U.S. Pat. No. 4,925,663 describes the use of inter alia a dry powder formulation comprising powdered rice, and a certain strain of a fungus, *Beauveria bassiana*, which has a particular virulence against fire ants, when used in an open environment.

Meikle et al (2007) J. Econ. Entomol. 100:pp 1-10 describes the use of carnauba wax as a carrier of *Beauveria bassiana* spores (strain Bb05002 that is indigenous to France) in beehives to control varroa mites. The environment within the hive is reported as having a relative humidity (RH) of from 40% to 50%, apparently at temperatures from 33° C. to 36° C. It appears that the ambient environment within the beehive is not subject to wide extremes of RH and temperature inter alia because the bees actively regulate the temperature within.

WO 2006/121350 describes the provision of certain biologically pure cultures of strains of entomopathogenic fungi, such as *Beauveria bassiana* for controlling phytopathogenic insects for use against *Thysanoptera* (thrips), *Hemiptera* (white fly) and others. The compositions described therein appear to be applied to plants in the field as a wet spray.

It is an object of the present invention to overcome or at least reduce the drawbacks of conventional methods of treating grain storage areas for arthropod infestation. This and other objects will become apparent from the following description and examples.

According to the present invention there is provided a dry powder composition that is effective in controlling populations of grain storage arthropods that comprises i) hydrophobic particles that adhere to the cuticle of one or more species of grain storage arthropod; and ii) spores of an entomopathogenic fungus that adhere to the said particles and that are capable of germinating on the cuticles of the one or more species of grain storage arthropod.

Without the intention of being bound by theory, it is thought that the particles that adhere to the arthropod cuticle do so via electrostatic forces operating between the particles which are electrostatically charged and the insect cuticle. Such particles are typically dielectric particles and are thought to maintain their electrostatic charge through the generation of electrical forces made by the rubbing of moving parts of the arthropod.

The particles of use in the invention possess a degree of hydrophobicity wherein the hydrophobic forces between the spores and arthropod cuticle are greater than the electrostatic forces between the spores and particles of use in the invention, hence the spores are able to detach from the said particles and then attach preferentially to the arthropod cuticle.

Thus, the spores of the entomopathogenic fungus for use in the invention possess an hydrophobicity that is different to the hydrophobicity associated with the hydrophobic particles. Preferably still, the hydrophobicity of the spores is also different to that of the grain storage arthropod cuticle such that the spores preferentially adhere to the cuticle of the at least one species of grain storage arthropod. Thus, the degree of hydrophobicity of the spores is typically greater than the hydrophobicity of the hydrophobic particles of use in the invention which in turn have a degree of hydrophobicity that is greater than the hydrophobicity of the arthropod cuticle. Thus, the degree of hydrophobicity of the spores of use in the invention can be presented as:

Spore hydrophobicity>hydrophobicity of the hydrophobic particles of use in the invention>hydrophobicity of the arthropod cuticle. Naturally, the skilled artisan will appreciate that put differently; the degree of hydrophilicity of the spores is lower than the hydrophilicity of the particles, which in turn have a higher degree of hydrophilicity than that of the arthropod cuticle. In order to test the degree of hydrophobicity of the representative components of use in the invention as outlined above, and hence their suitability for use in the present invention, the man skilled in the art is able to simply make a visual assessment of the ratio of spores:particle, and particle:arthropod cuticle or spores:particle:cuticle using commonly employed techniques such as employing an Electron Scanning Microscope. Typically, the hydrophobic particles of use in the invention carry the spores to the grain storage arthropod cuticle placing them in contact therewith, or the charged particles bring the spores into close proximity with the arthropod cuticle surface where the spores become detached from the carrying particle due to the differences in hydrophobicity between the carrying particle and the spore, and adhere preferentially to the cuticle surface. Once the spores of the invention are delivered to the cuticle they are capable of germination on the cuticle of said at least one species of grain storage arthropod, and of penetrating the cuticles thereof.

By making use of the hydrophobicity of the spores and of the electrostatic attraction of the carrier particles of use in the invention an efficient carrier system is achieved that is able to carry spores to target insect cuticle surfaces. The fungus spores themselves may then be deposited on the insect cuticle where the spores then germinate and penetrate the insect cuticle. In cases where the spores are not sufficiently attracted to the insect cuticle through hydrophobic forces but remain on the particles that adhere to the arthropod cuticle surface, the fungus spores on the carrier particle should be capable of germinating on or near to the surface of the insect cuticle and capable of penetrating it.

The dry powder compositions of the invention may also contain suitable excipients commonly employed in the art such as flow agents or anti-caking agents selected from sodium bicarbonate, sodium ferrocyanide, potassium ferrocyanide, calcium ferrocyanide, bone phosphate, sodium silicate, silicon dioxide, calcium silicate, magnesium trisilicate, talcum powder, sodium aluminosilicate, potassium aluminium silicate, calcium aluminosilicate, bentonite, aluminium silicate, stearic acid, polydimethylsiloxane and the like.

Additionally, dry powder compositions of the invention may contain other components such as additives selected from UV blockers such as beta-carotene or p-aminobenzoic acid, colouring agents such as optical brighteners and commercially available colouring agents, such as food colouring agents, plasticisers such as glycerine or soy oil, antimicrobials such as potassium sorbate, nitrates, nitrites, propylene oxide and the like, antioxidants such as vitamin E, butylated hydroxyl anisole (BHA), butylated hydroxytoluene (BHT), and other antioxidants that may be present, or mixtures thereof. The skilled artisan will appreciate that the selection of such commonly included additives will be made depending on end purpose, and perceived need.

The dry powder compositions of the invention must be effective in controlling populations of grain storage arthropods. The entomopathogenic fungus spores (also referred to in the art as "conidia") of use in the invention must be capable of germinating on the cuticle of the at least one grain storage arthropod and once germinated, of penetrating the cuticle of recipient arthropods and killing them.

Suitable spores (conidia) of use in the present invention include those selected from strains of the entomopathogenic fungus species *Beauveria bassiana, Paecilomyces fumosoroseus* and *Lecanicillium* spp.

Preferred entomopathogenic fungus strains for acquiring spores or conidia of use in compositions of the invention include those selected from the species *Beauveria bassiana*. Most preferably, a strain of *Beauveria bassiana* suitable for use in providing spores or conidia of use in the invention is the strain deposited under the Budapest Treaty, IMI 398548, deposited at the Centre for Agriculture and Biosciences International (CABI), Bakeham Lane, Egham, Surrey, TW20 9TY, UK on 11 May 2010.

The *Beauveria bassiana* spores of use in the invention must be capable of germinating, and once germinated, of penetrating the cuticle of grain storage arthropods, such as grain storage beetles. Preferably, the *Beauveria bassiana* strains of use in the invention are active against at least the following species of grain storage beetle: *Oryzaephilus surinamensis* (saw-toothed grain beetle), *Sitophilus granarius* (grain weevil), and *Cryptolestes ferrugineus* (rust-red grain beetle.

The "one or more grain storage arthropod" refers to grain storage arthropods that are insects, such as grain storage beetles or moths and/or their larvae that inhabit grain storage areas. Examples of such grain storage beetle species include *Oryzaephilus surinamensis* (saw-toothed grain beetle), *Sitophilus granarius* (grain weevil), and *Cryptolestes ferrugineus* (rust-red grain beetle).

"Grain storage areas" for the purposes of the present invention includes dried food and/or grain storage sites such as grain silos and grain bins where dried food or grain is stored immediately after harvest or prior to processing and includes warehouses where dried food and grain is stored prior to shipment, and transport facilities such as those of shipping containers, the holds of ships, trucks, aeroplanes, storage areas in supermarkets, dried food holding centres and the like. The term "grain storage area" includes within its ambit those storage areas in which harvested grain products such as wheat, rye, barley, corn, and sorghum grains, and dried foods derived from harvested grain or harvested seed such as flours, dried beans, lentils, pulses, rice and other foodstuff commodities such as dried pasta derived from grain and/or other dried foodstuffs are held.

For the purposes of the present invention "controlling populations of grain storage arthropods" means that the arthropod population to which compositions of the invention are applied are ones that suffer losses due to death, ill health that may ultimately lead to death, and/or inability to reproduce or reduction in the ability to reproduce. Preferably, the controlling of populations of storage arthropods means that at least 80%, preferably 90%, of the population of arthropods dies within 28 days of application of compositions of the invention. Preferably, the populations of arthropods that are adversely affected by compositions of the invention die or at least suffer sub-lethal effects which contribute to long-term population reduction as a result of the application of dry powder compositions of the invention to the grain storage area. The man skilled in the art will appreciate that the population of grain storage arthropods to which the compositions of the invention are applied may be made up of one or more than one species of arthropods. Examples of species of arthropods that may make up a population of grain storage arthropods that may be affected by compositions of the invention include grain storage beetles such as *Oryzaephilus surinamensis* (saw-toothed grain beetle), *Sitophilus granarius* (grain weevil), and *Cryptolestes ferrugineus* (rust-red grain beetle).

The hydrophobic composite particles of the invention typically comprise waxes having a melting point of ≥50° C., more preferably of ≥60° C. and most preferably are made up of hard waxes having a melting point of ≥70° C. Suitable waxes of use in the invention include carnauba wax, bees wax, Chinese wax, shellac wax, spermaceti wax, candelilla wax, castor wax, ouricury wax, and rice bran wax.

In a preferment of the invention there is provided a dry powder composition that is effective in controlling populations of grain storage arthropods that comprises i) hydrophobic particles that adhere to the cuticle of one or more species of grain storage arthropod; and ii) spores of an entomopathogenic fungus that adhere to the said particles and that are capable of germinating on the cuticles of the one or more species of grain storage arthropod. Preferably, dry compositions of the invention comprise particles having a volume mean diameter of ≥10 µm, and more preferably dry compositions of the invention have a volume mean diameter of ≥12 µm. Such compositions having a volume mean diameter of ≥10 µm are not considered to be as great a thoracic hazard as particles of a smaller size, and are not thought to pose as great an allergenic threat to humans.

As a further aspect of the invention, there is provided a composite particle for use in a composition of the invention that comprises i) a hydrophobic particle that adheres to the cuticle of at least one species of grain storage arthropod; and ii) spores of an entomopathogenic fungus that adhere to the said particles and that are capable of germinating on the cuticles of the at least one species of grain storage arthropod. Preferably, the volume mean diameter of the composite particle is ≥10 µm, and more preferably ≥12 µm. To make composite particles of the invention, the spores of the entomopathogenic fungus may be admixed with the hydrophobic particles, such as particles of carnauba wax, at a weight ratio of from 5-95% by weight of hydrophobic particles to spores, preferably at a weight ratio of at least 50 to 80% by weight of hydrophobic particles to spores, or more preferably of at least 75% by weight of hydrophobic particles to spores. The particles may be preferably micronised to a VMD of ≥34 µm to maintain formulations within safe VMD limits. The skilled addressee will appreciate that other ratios of hydrophobic particles:spores could be employed to make composite particles of the invention depending on the hydrophobic particle size and its physical properties, such as electrostatic properties.

The composite particles of the invention may also contain suitable excipients commonly employed in the art such as flow agents or anti-caking agents selected from sodium bicarbonate, sodium ferrocyanide, potassium ferrocyanide, calcium ferrocyanide, bone phosphate, sodium silicate, silicon dioxide, calcium silicate, magnesium trisilicate, talcum powder, sodium aluminosilicate, potassium aluminium silicate, calcium aluminosilicate, bentonite, aluminium silicate, stearic acid, polydimethylsiloxane and the like.

Additionally, composite particles of the invention may contain other components such as additives selected from UV blockers such as beta-carotene or p-aminobenzoic acid, colouring agents such as optical brighteners and commercially available colouring agents, such as food colouring agents, plasticisers such as glycerine or soy oil, antimicrobials such as potassium sorbate, nitrates, nitrites, propylene oxide and the like, antioxidants such as vitamin E, butylated hydroxyl anisole (BHA), butylated hydroxytoluene (BHT), and other antioxidants that may be present, or mixtures thereof. The skilled artisan will appreciate that the selection of such commonly included additives will be made depending on end purpose, and perceived need.

Compositions of the invention wherein at least 50% by volume of the composition is ≥10 µm are thought to be less of a thoracic respiration hazard and to be less allergenic to humans. Furthermore, by using compositions of the invention, an efficient means of delivering higher numbers of fungal spores of interest to the target populations of grain storage arthropods and to the cuticles thereof than has hitherto been achieved, is possible.

In a further aspect of the invention there is provided a method of producing compositions of the invention comprising the steps of
i) micronising dry hydrophobic carrier particles; and
ii) admixing dry spores of *Beauveria bassiana* with the said carrier particles.

In a further aspect of the invention there is provided a method of controlling grain storage arthropod infestation in a grain storage area wherein composite particles according to the invention are presented to the surfaces of a grain storage area by
i) collecting the composite particles in a dusting apparatus;
ii) releasing the said particles from the said dusting apparatus and into the said grain storage area.

In another aspect of the invention there is provided a method of controlling grain storage arthropod infestation in a grain storage area wherein a dry powder composition according to the invention is presented to the surfaces of a grain storage area.

In a still further aspect of the invention there is provided use of a composite particle according to the invention in the control of grain storage arthropod infestation in grain storage areas.

In yet a still further aspect of the invention there is provided use of a dry powder composition of the invention in the control of grain storage arthropod infestation in grain storage areas.

A biologically pure culture of a novel isolate of *Beauveria bassiana* has been deposited with CABI, Bakeham Lane, Egham, Surrey, TW20 9TY, UK on 11 May 2010 in accordance with the Budapest Treaty for the deposit of microorganisms and accorded the deposit number of IMI 398548.

There now follow examples and figures illustrating the invention. It is to be understood that the teaching of the examples and figures is not to be construed as limiting the invention in any way.

EXAMPLES SECTION

1. Outline

This section contains details about:
  Why carnauba wax particles are selected as a suitable carrier for *B. bassiana* spores designed for use against grain storage arthropods such as grain storage beetles.
  How the biopesticide formulations are made
  Where the materials are sourced from
  Efficacy testing of the formulations in the field 2. Summary The use of carnauba wax in admixture with *B. bassiana* (Bb) spores, isolate IMI 398548, for the control of storage pests in stored grain and for processing environments is a particularly useful combination because:
  Spores alone are small enough to be a respiratory hazard but the inclusion of carnauba wax particles at certain particle volume mean diameters to the spores increases the mean particle size diameter above the hazard threshold.
  Spores adhere to the exterior of carnauba wax particles and become co-located. Co-location was observed to be significantly lower when spores were mixed with other powdered particles of a similar particle size range.
  Carnauba wax particles adhere to insect cuticles via electrostatic attraction, thus carnauba wax transports spores to the arthropod site of infection.
  When a spore:carnauba wax composite particle adheres to an insect, the spores are observed to detach from the carnauba wax particle and attach preferentially to the arthropod cuticle, thus the spores are 'delivered' to the arthropod cuticle by the carnauba wax particle component of the composite particle.
  When tested in a grain store environment, a carnauba wax particle:Bb isolate (IMI 398548) formulation resulted in higher mortality levels of three target grain storage arthropod pests (grain storage beetles) than an oil based formulation with the same concentration of spores.

3. Introduction

These studies formed part of a research program to develop the use of fungal spores to reduce chemical pesticide in storage and food process environments. The main objective of this program was to develop a pathogen-based crack and crevice formulation to be used as an empty food or storage bin treatment. Instead of conventionally applying fungal spores directly into cracks and crevices, this research program investigated the prospects of using carriers, including an inert powder, carnauba wax particles (Exosect Ltd, Winchester, UK), for delivery of the fungal spores. Micronised carnauba wax powder exhibits electrostatic properties and has been shown to adhere to charged insect cuticles via electrostatic attraction.

4. Carnauba Wax as a Carrier for a Grain Mycopesticide

This project shows that for the isolates to control pests under conditions representing those in (grain) storage areas, it is essential to improve the uptake by the pests of the fungal spores, their germination on arthropod pests and their penetration thereinto. Bb spores also represent a significant respiratory hazard if they are used alone, because the volume mean diameter of dry spores is only 2-3 μm. It has been shown that a dust sample comprising 50% by volume of particles with an aerodynamic diameter of ≤10 μm represents a significant thoracic dust hazard, and those with 50% at ≤4 μm represents a significant respirable hazard (British Standards Institution EN481,1993). The hazard represented by Bb spores is higher than that of an inert dust due to the proteinaceous nature of the material making them inhalable allergens (Westwood et al. 2005). It is therefore important to investigate delivery systems and potential carriers of the spores, which could enhance their uptake and retention on arthropod pests and their safe use. Carnauba wax, if mixed with the spores, could, by means of electrostatic attraction, enhance uptake and retention of fungal spores by storage pests, while also increasing the mean particle size of the admixture above the threshold for a respirable hazard, 50% by volume of the carnauba wax particles is always >10 μm, as measured by laser diffraction of repeat batch analysis at Exosect Limited.

4.1. Work Conducted by Exosect

We have made an assessment of the suitability of carnauba wax particles as a carrier for Bb spores compared to other powders. We assessed the adherence of the spores to the carnauba wax powder particles under scanning electron microscope (SEM). Diatomaceous earth (DE) and kaolin clay were selected for comparison with carnauba wax particles as these comprise fine particulate matter used currently in conventional methods of insect control. The ability of spores to adhere to each of the powders was assessed under SEM. The ability of the powder and spore mixes to then adhere to beetle cuticles were assessed by examining treated beetles, *O. surinamensis*, under SEM.

DE and Kaolin clay were either mixed directly with dry attenuated Bb isolate (IMI 398548) or they were formulated with coatings of stearic acid or carnauba wax (molten carnauba wax) by melting the components in a vessel, cooling, and then micronising in a mill using methods known in the art. All seven powder types were mixed with fungal spores at a ratio of 5:1 (w/w) and examined under SEM. Then, ten beetles (of *O. surinamensis*) were exposed for 48 h in Petri dishes to 10 g of rolled oats containing 0.15 g of a carnauba wax particle and spore mixture at a ratio of 2:1 (w/w). The beetles were then removed to clean rolled oats for 24 h and then examined under SEM.

Figure 1:
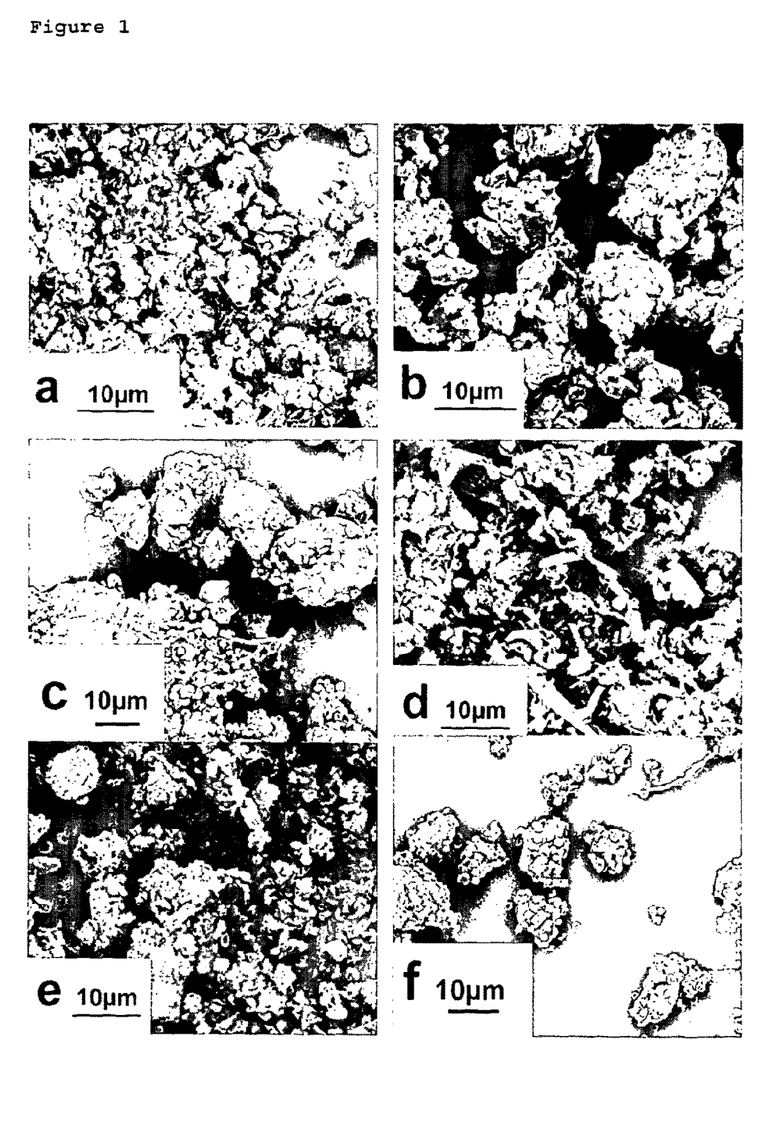
FIG. 1: Scanning electron microscope images of *Beauveria bassiana* isolate IMI 398548 spores admixed with (a) kaolin, (b) kaolin coated with stearic acid, (c) kaolin coated with carnauba wax, (d) diatomaceous earth, (e) diatomaceous earth coated with stearic acid and (f) diatomaceous earth coated with carnauba wax. Spores are identifiable as 2-3 µm concave discs.

Kaolin clay powder and DE particles used in the studies was comprised of variable sizes (from 1-5 μm diameter) and were of irregular shape. Few spores were observed adhering to the exterior of the kaolin or DE particles; many spores remained loose within both the mixtures (FIGS. 1a and 1d). When kaolin and DE were formulated with a coating of stearic acid, particle size was increased and the mixtures became clumpy but adherence of the spores appeared improved (FIGS. 1b and 1e). A coating of carnauba wax particles caused the kaolin powder to form large clumps with some particle sizes>100 μm; however, spores were seen to adhere all over the exterior of these particles. When DE was coated in carnauba wax, particle size was increased, but it was not as clumpy as the carnauba wax-coated kaolin; the spores adhered well to the coated particles (FIGS. 1c and 1f). Spore adherence was better when kaolin and DE were coated with carnauba wax than with stearic acid. All these coated formulations would require additional processing to reduce particle size and clumping.

Figure 2:
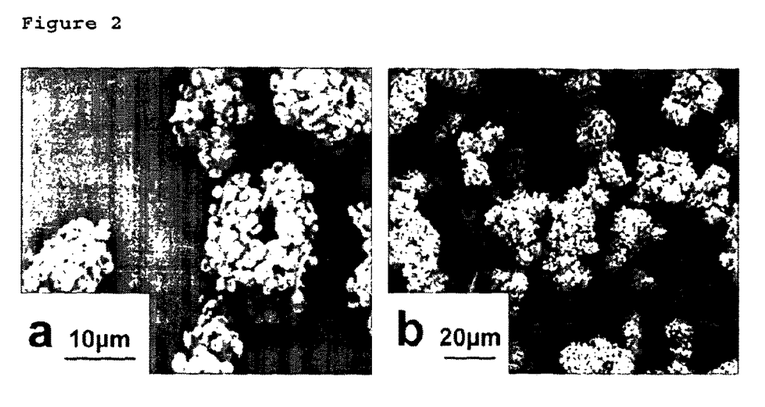
FIG. 2: Scanning electron microscope images of *Beauveria bassiana* isolate IMI 398548 spores admixed with (a and b) carnauba wax particles. Spores are identifiable as 2-3 μm concave discs.

When carnauba wax particles alone were mixed with the spores, the spores were observed to adhere all around the outer surfaces of the wax particles (FIGS. 2a and 2b) and no further processing to reduce particle size would be required. The % surface area of carrier powder covered by the spores was estimated to be around <5% for kaolin and DE, 10-20% for carnauba-coated kaolin and DE, and 50% for carnauba wax alone. Carnauba wax alone resulted in the best coverage by the spores and this was also the easiest formulation to make because it was directly admixed without first applying a coating.

When the grain storage beetles were treated with the spore and carnauba wax mix, spores and carnauba wax particles were both easily identified adhering to the cuticles of *O. surinamensis*, particularly in cuticle indentations and structures such as sensilla pits (FIGS. 3a and 3b). We also observed that the spores were no longer adhering to the exterior of the carnauba wax particles but appeared now to be adhering directly to the insect cuticle.

Figure 3:
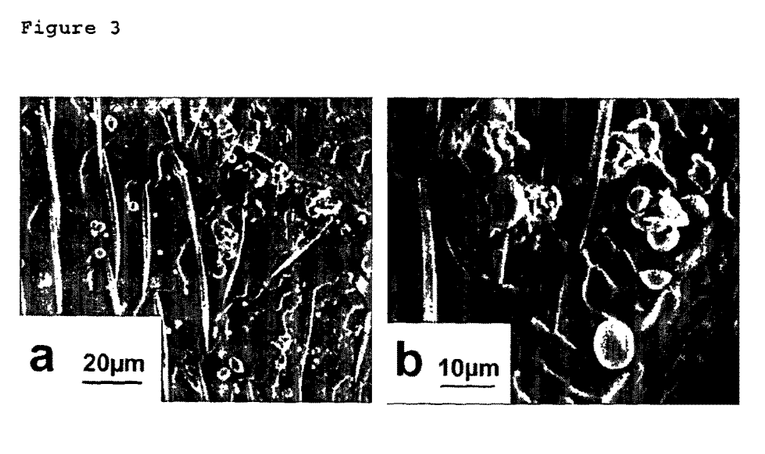
FIG. 3: Scanning electron microscope images of *Oryzaephilus surinamensis* cuticle after exposure to rolled oats treated with an carnauba wax particles and *Beauveria bassiana* isolate IM1389521 spore mixture (a and b). Carnauba wax particles and spores can be clearly seen adhering to the insect cuticle, particularly around the sensilla pits. Carnauba wax particles are identifiable as 2-10 μm irregular particles and spores as 2-3 μm concave discs.

In conclusion, the affinity of the Bb spores and carnauba wax particles provide evidence that carnauba wax could act as a suitable carrier for the spores, and would be superior to other powders with similar particle size ranges. The SEM images of *O. surinamensis* treated with a carnauba wax and spore admixture showed that the spores detached from the carnauba wax particles and attached to the insect cuticle. Thus, despite the excellent level of adherence of spores to carnauba wax particles, the spores clearly had a greater affinity for the insect cuticle than the carnauba wax particles. Boucias et al. (1988) demonstrated that hydrophobicity of the insect cuticle and conidial wall appeared to mediate adhesion rather than electrostatic forces. The ability of a carrier powder to co-locate with the spores and then to detach from spores when in contact with the insect are desirable attributes of a spore delivery system.

Making the Carnauba Wax Based Formulation

For the purposes of determining the optimum formulation composition Exosect investigated the effect of carnauba wax particle volume mean diameter (VMD) and ratio of carnauba wax to attenuated spores on the final VMD of the mixture. The purpose of the study was to determine formulation compositions that would fall within safe VMD limits. Three speeds were selected which resulted in carnauba wax batches with VMDs of 15.12, 34.14 and 62.33 μm. Attenuated (oven heated) *Beauveria bassiana* spores of strain IMI 398548 were supplied by CABI (Bakeham Lane, Englefield Green, Egham, Surrey TW20). Each batch of carnauba wax was mixed with spores at ratios (w/w) of 3:1, 1:1 and 1:3 in separate sample vials. Three replicate samples were created for each formulation. The particle VMD and X50 measurement (diameter of particles that 50% of the particles are equal to or less than) of each sample, as well as replicate samples of the plain carnauba wax batches and the plain spores, were measured using laser diffraction at a pressure of 4 mbar (Sympatec: RODOS attached to HELOS H2098).

Figure 5:
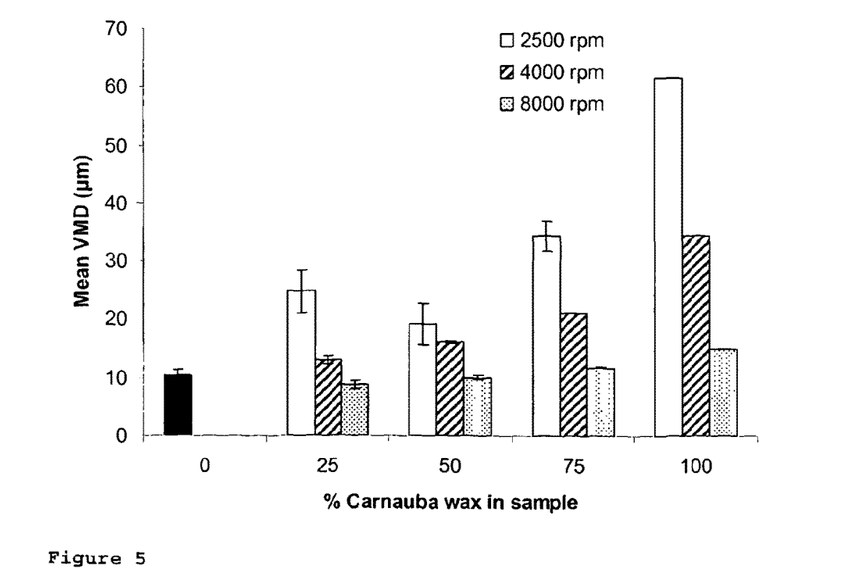
FIG. 5: Mean volume mean diameters (VMD) of carnauba wax powder/spore formulations with different ratios of wax to spores and with wax micronised at different speeds. The black bar represents the plain spores (0E—no carnauba wax). Closed bars represent standard errors.

The mean VMD of each formulation type was calculated from the three replicates (FIG. 5). Plain spore samples with particles of diameter 2.49±0.0173 μm, as indicated by the X50 (up to 50% of the spores had a particle size≤2.49±0.0173 μm), actually had a VMD mean of 10.41 μm±0.97 μm due to the presence of a few clumps, however, this is very close to the thoracic breathing hazard limit of 10 μm, indicating that spores by themselves could present a significant breathing hazard. It was clear from the analysis that the inclusion of carnauba wax powder increased the VMD compared to plain spores.

The VMD raw data were log transformed to normalise them then an analysis of variance (ANOVA) with factors for mill speed and carnauba wax percentage was applied to the data. The ANOVA was followed by Tukey pairwise comparisons when significant effects occurred to determine differences between treatment groups. The analysis indicated that there were significant differences in the VMD between one or more treatment groups. There was a significant effect of micronisation speed and carnauba wax percentage on the VMD of the formulation (ANOVA: $F_{2,35}$=144.245, P<0.001 and $F_{3,35}$=144.245, P<0.001 respectively). There was no statistically significant difference in the VMD between formulations that had 25 or 50% carnauba wax in them, but the VMD of formulations with 75% carnauba wax was significantly greater. Formulations that were made with carnauba wax micronised at 2500, 4000 or 8000 rpm were all significantly different from each other, with the slowest mill speed of 2500 rpm resulting in the formulations with the largest VMD.

The data indicates that the mill speed and % carnauba wax can be used to control the VMD of the final formulation. There were smaller differences between formulations micronised at the fastest mill speed of 8000 rpm compared to the slowest micronisation speed of 2500 rpm. There was not much of a difference in VMD between formulations that contained 25 or 50% carnauba wax. Adding 25% carnauba wax to spores increased the VMD from 10.41 μm to >13 μm as long as the wax was micronised at 4000 rpm or slower, for 50% this VMD was >15 μm and for 75% this VMD was >20 μm.

It is recommended that carnauba wax powder for the grain biopesticide formulations is milled at 4000 rpm, because using carnauba wax milled at 8000 rpm did not increase the VMD significantly compared to plain spores, even when 75% carnauba wax was used. The spores have a much stronger influence on the VMD than the carnauba wax because they are less dense and therefore for the same weight they occupy approximately three times as much volume (visual estimate) as the carnauba wax. If efficacy can be retained by using higher concentrations of carnauba wax (e.g. 75% wax compared to 25%) then this will reduce the breathing hazard posed by the formulation. It is also likely that increasing the carnauba wax concentration will be of benefit to product application by bulking up the product at the same spore concentration thus making it easier to apply evenly over the same surface area.

The spores may be admixed to the carnauba wax at 5-95% by weight of the final product, preferably of at least 50% by weight of carnauba wax, or more preferably of at least 75% by weight of carnauba wax micronised to a VMD of ≥34 μm to maintain formulations within safe VMD limits.

5. Suppliers of Materials

The Bb isolate IMI 398548 is deposited with CABI as hereinbefore described.

Carnauba wax particles of use in the invention are manufactured by grinding unrefined carnauba wax (available from The British Wax Refining Co. Ltd., 62 Holmethorpe Avenue, Holmethorpe Industrial Estate, Redhill, Surrey, UK), milling it, followed by a micronisation step using techniques commonly employed in the art.

6. Field Efficacy Testing 6.1. Method

A pilot scale trial of an oil based and the carnauba wax based biopesticide formulation was conducted.

The aim of the trial was to assess the formulations against three species of insect (*Oryzaephilus surinamensis* strain Tram (saw-toothed grain beetle), *Sitophilus granarius* strain Gainsborough (grain weevil) and *Cryptotestes ferrugineus* strain C124 (rust-red grain beetle)) when applied to arenas made of plywood in the grain store environment. It was necessary to examine the effect of the two formulations when applied at similar concentrations: $2.5\times10^{10}$ conidia/$m^2$ and $5.1\times10^{10}$ conidia/$m^2$. In addition, the viability of the conidia in the two formulations under typical UK grain store conditions was assessed. A comparison with a currently registered chemical pesticide, pirimiphos methyl (Actellic), was also made. The dust formulation was weighed out and the appropriate amount was evenly distributed across the floor area of the assigned arena rings using a small brush. The oil formulation and reference pesticide were applied using calibrated sprayers. There were five replicate arenas for each treatment and control. Fifty insects of each species were added to each arena 24 h after treatment and then mortality in each arena was assessed 14 and 28 days after the addition of the insects. Dead insects were surface sterilized with sodium hypochlorite solution, maintained in a damp environment and examined after 3-4 days for evidence of mycosis to prove whether or not mortality was due to the Bb treatment. Temperature and humidity were monitored throughout the experiment.

6.2 Results

The results are depicted in FIG. 4 and Table 1 (below).

TABLE 1

Derived mean % mortality of insects 28 days after exposure to different treatments. % mortality is expressed in terms of the cumulative number of dead insects recovered after 14 and 28 days divided by the total of the number of insects recovered after 28 days and the number of dead insects after 14 days. Figures in parentheses are the derived 95% confidence intervals. (A) Comparison of treatments and controls for the biopesticide formulations. Oil blank is the oil carrier without conidia. Dust blank is carnauba wax alone (referred to as Entostat ® in FIG. 4).

| | Mean % mortality* | | |
|---|---|---|---|
| | *S. granarius* | *O. surinamensis* | *C. ferrugineus* |
| Control (no treatment) | 1.7 a<br>(0.3, 9.5) | 11.4 a<br>(4.5, 26.1) | 8.7 a<br>(3.5, 20.2) |
| Oil blank | 4.7 a<br>(1.6, 13.2) | 12.4 a<br>(5.3, 26.4) | 26.0 b<br>(15.7, 39.9) |
| Dust blank | 5.8 a<br>(2.2, 14.2) | 9.3 a<br>(3.4, 22.8) | 21.5 a, b<br>(12.1, 35.3) |
| Oil $2.5 \times 10^{10}/m^2$ | 53.6 b<br>(42.2, 64.6) | 45.3 b<br>(30.5, 61.0) | 79.2 c<br>(65.9, 88.2) |
| Oil $5.1 \times 10^{10}/m^2$ | 56.5 b<br>(44.9, 67.3) | 52.5 b<br>(37.4, 67.2) | 79.8 c<br>(66.1, 88.9) |
| Dust $2.5 \times 10^{10}/m^2$ | 90.6c<br>(81.4, 95.5) | 83.1 c<br>(68.4, 91.8) | 94.1 d<br>(83.5, 98.1) |
| Dust $5.1 \times 10^{10}/m^2$ | 90.9 c<br>(82.1, 95.6) | 79.8 c<br>(64.8, 89.4) | 95.1 d<br>(84.6, 98.6) |

*In each column means followed by the same letter are not significantly different (GLM, $P > 0.05$)

The isolate IMI 398548 showed a good level of viability (90.6% germination) and no contaminants were present.

The average temperature recorded in the grain store throughout the trial was 16.0° C. with a minimum of 6.7° C. and a maximum of 24,4° C. The average humidity during the trial recorded was 77.1% with a minimum of 45.2% and a maximum of 96.0%.

The viability of the conidia in both the oil and dust formulations remained very high throughout the duration of the trial, with greater than 80% germination observed for both formulations recovered from the treated plywood squares.

At 14 days post exposure:

There was a highly significant effect of treatment on mortality for all three species after 14 days exposure (GLM, $F_{6,34}=26.65$, $P<0.001$, $F_{6,34}=18.57$, $P<0.001$ and $F_{6,34}=28.25$, $P<0.001$ for *S. granarius, O. surinamensis* and *C. ferrugineus* respectively).

There was no effect of the carrier controls on mortality.

Mortality of *S. granarius* and *C. ferrugineus* with both the oil and the dust spore formulations at either concentration was significantly greater in comparison to the untreated and carrier treatments.

Mortality of *O. surinamensis* for the oil formulation containing $5.1\times10^1$ conidia/$m^2$ and for both concentrations of the carnauba wax formulation was significantly higher than that for the no treatment or carrier controls.

Treatment with the carnauba wax: spore formulations resulted in significantly greater mortality for *S. granarius* and *O. surinamensis* compared with the oil spore formulations at either concentration.

The pesticide reference treatment resulted in significantly higher mortality than all other treatments.

At 28 days post exposure:

There was a highly significant effect of treatment on mortality for all three species after 28 days exposure (GLM, $F_{6,34}$=60.31, P<0.001, $F_{6,34}$=20.25, P<0.001 and $F_{6,34}$=35.47, P<0.001 for *S. granarius, O. surinamensis* and *C. ferrugineus* respectively).

There was no effect of the carrier controls on mortality except for oil on *C. ferrugineus*.

Both the oil and the carnauba wax spore formulations at either concentration caused significantly higher mortality of all three species in comparison to the untreated and carrier controls.

There were significant differences between the Entostat and oil spore formulations at both concentrations for all of the three species tested at the 5% probability level.

The pesticide reference treatment resulted in significantly higher mortality than all other treatments.

Subsequent examination of dead insects confirmed that the majority of deaths in the spore formulation treatments were caused by mycosis but deaths in the pesticide and control treatments were not due to mycosis. This shows that the Bb was responsible for death in the relevant treatments.

6.3 Summary

Figure 4:
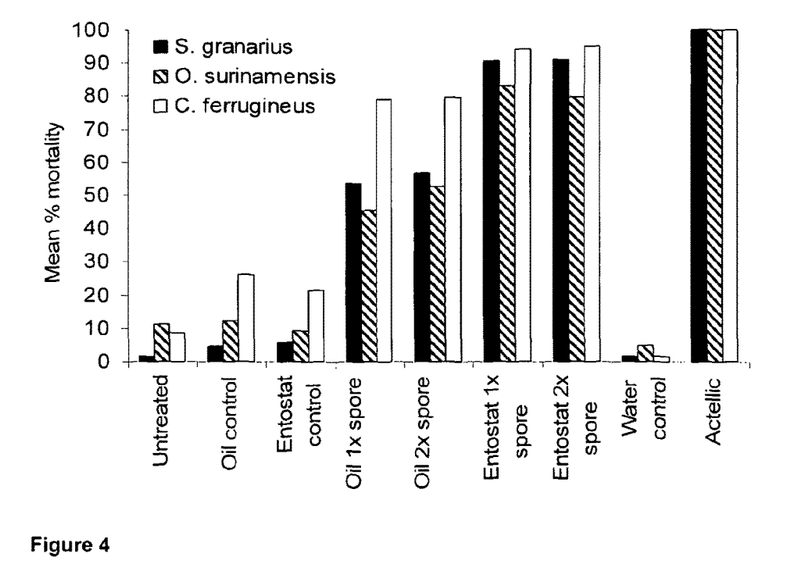
FIG. 4: Mean % grain beetles, of three species, dead in each treatment category at 28 days post exposure to treatments.

In summary, the oil and carnauba wax based spore formulations caused significantly higher mortality than any control treatments, but not as high as the pesticide reference treatment (which caused 100% mortality as expected). The carnauba wax based formulation with the highest concentration caused between 80-95% mortality for the three species tested at 28 days post exposure (FIG. 4). In general, the carnauba wax based formulations gave a greater level of control than the oil formulations. Both formulations retained a good level of viability under typical UK grain store conditions for up to 28 days.

7. References

Armsworth, C. G., I, H. Baxter, L. E. E. Barton, G. M. Poppy, and C. Nansen. 2006. Effects of adhesive powders on the mating and flight behavior of Mediterranean fruit fly (Diptera: Tephritidae). Journal of Economic Entomology 99, 1194-1202.

Armsworth, C. G., C. D. Rogers, L. E. E. Barton, C. Soares, and G. M. Poppy. 2008. Uptake of adhesive powders from lure stations by Mediterranean fruit fly (Dipt., Tephritidae). J. Appl. Entomol. 132: 45-53.

Barton, L. E. E., Armsworth, C. G., Baxter, I. H., Poppy G. M., Gaunt, L. F., Nansen, C., 2006. Adhesive powder uptake and transfer by Mediterranean Fruit Flies, *Ceratitis capitata* (Diptera: Tephritidae). Journal of Applied Entomology 130, 257-262.

Baxter, I. H. 2008 Entomopathogen based autodissemination for the control of *Plodia interpunctella* (Hübner)—an examination of the critical components. PhD Thesis University of Southampton.

Baxter, I. H., N. Howard, C. G. Armsworth, L. E. E. Barton, and C. Jackson. 2008. The potential of two electrostatic powders as the basis for an autodissemination control method of *Plodia interpunctella* (Hübner). J. Stored Prod. Res. 44:152-161.

Boucias D. G., Pendland J. C. & Latge J. P. 1988. Nonspecific factors involved in attachment of entomopathogenic Deuteromycetes to host insect cuticle. Applied and Environmental Microbiology, 54, 1795-1805.

British Standards Institution (1993) BS EN 481:1993 Workplace atmospheres. Size fraction definitions for measurement of airborne particles. ISBN 0 580 22140 7.

Howse, P. E., and K. L. Underwood. 2000. Environmentally-safe pest control using novel bioelectrostatic techniques: initial results and prospects for area-wide usage, pp. 295-299. In K. H. Tan (ed.), Area-wide control of fruit flies and other insects. Penerbit University Sains Malaysia, Penang.

Meikle, W. G., G. Mercadier, N. Hoist, C. Nansen, and V. Girod. 2007. Duration and spread of an entomopathogenic fungus, *Beauveria bassiana* (Deuteromycota: Hyphomycetes), used to treat varroa mites (Acari: Varroidae) in honey bee (Hymenoptera: Apidae) hives. J. Econ. Entomol. 100: 1-10.

Nansen, C., MacDonald, K. M., Rogers, C. D., Thomas, M., Poppy, G. M., Baxter, I. H., 2007. Effects of sex pheromone in electrostatic powder on mating behaviour by Lobesia botrana males. Journal of Applied Entomology 131, 303-310.

Nansen, C., Barton, L. E. E. & Nansen, M. 2007. Uptake, retention, and repellency of a potential carrier of active ingredients in crack and crevice treatments for stored-grain beetles. Journal of Stored Products Research. vol. 43, no 4, pp. 417-424.

Westwood, G. S., Huang, S. & Keyhani, N. O. 2005. Allergens of the entomopathogenic fungus *Beauveria bassiana*. Clinical and Molecular Allergy 3.

The invention claimed is:

1. A method of using a composite particle for control of grain storage pests comprising:
    applying a plurality of composite particles to a grain storage facility,
    wherein said composite particle consists essentially of:
    i) a hydrophobic particle that adheres to the cuticle of at least one species of a grain storage arthropod; and
    ii) an effective amount of spores of an entomopathogenic fungus *Beauveria bassiana*, strain IMI 398548, that adhere to the hydrophobic particle and are capable of germinating on the cuticle of the at least one species of a grain storage arthropod and providing an effective mortality for said species when germinated.

2. The method according to claim 1, wherein the hydrophobic particle is a wax having a melting point≥50° C.

3. The method according to claim 1, wherein the hydrophobic particle is a wax having a melting point≥60° C.

4. The method according to claim 1, wherein the hydrophobic particle is a wax selected from carnauba wax, bees wax, Chinese wax, shellac wax, spermaceti wax, candelilla wax, castor wax, ouricury wax and rice bran wax.

5. The method according to claim 1, wherein the hydrophobic particle is carnauba wax.

6. The method according to claim 1, wherein the one or more species of grain storage arthropod is an insect.

7. The method according to claim 1, wherein the one or more species of grain storage arthropod is selected from *Oryzaephilus surinamensis* (saw-toothed grain beetle), *Sitophilus granarius* (grain weevil) and *Cryptolestes ferruginus* (rust-red grain beetle).

8. The method according to claim 1, wherein the composite particle has a diameter of ≥10 μm.

9. The method according to claim 1, wherein the composite particle has a diameter of ≥12 μm.

10. A method of using a dry powder composition effective in controlling populations of grain storage arthropods comprising:
    applying a dry power composition to a grain storage facility, the composition comprising composite particles which consist essentially of:
    i) hydrophobic particles that adhere to the cuticles of one or more species of grain storage arthropod; and
    ii) an effective amount of spores of an entomopathogenic fungus *Beauveria bassiana*, strain IMI 398548, that adhere to the hydrophobic particles and are capable of germinating on the cuticles of the one or more species of grain storage arthropod and providing an effective mortality for said species when germinated.

11. The method according to claim 10, wherein the composite particles have a volume mean diameter of ≥10 µm.

12. The method composition according to claim 10, wherein the composite particles have a volume mean diameter of ≥12 µm.

13. The method according to claim 10, wherein the weight of the hydrophobic particles is 50 to 80% by weight of the composite particles.

14. A method of using a composite particles for the control of grain storage pest comprising:
   applying a plurality of composite particles to a grain storage facility,
   wherein said composite particles consist essentially of:
   i) a hydrophobic particle that adheres to the cuticle of at least one species of a grain storage arthropod;
   ii) an effective amount of spores of an entomopathogenic fungus *Beauveria bassiana*, strain IMI 398548, that adhere to the hydrophobic particle and are capable of germinating on the cuticle of the at least one species of a grain storage arthropod and providing an effective mortality for said species when germinated, and
   iii) a flow agent.

15. The method according to claim 14, wherein the hydrophobic particle is a wax having a melting point≥50° C.

16. The method according to claim 14, wherein the hydrophobic particle is a wax selected from carnauba wax, bees wax, Chinese wax, shellac wax, spermaceti wax, candelilla wax, castor wax, ouricury wax and rice bran wax.

17. The method according to claim 14, wherein the hydrophobic particle is carnauba wax.

18. The method according to claim 14, wherein the one or more species of grain storage arthropod is an insect.

19. The method according to claim 14, wherein the composite particle has a diameter of ≥10 µm.

20. The method according to claim 14, wherein the composite particle has a diameter of ≥12 µm.

* * * * *